US012721955B2

(12) United States Patent
Breatnach

(10) Patent No.: US 12,721,955 B2
(45) Date of Patent: Sep. 1, 2026

(54) MEDICAL DEVICE

(71) Applicant: Indomed Limited, Sandyford (IE)

(72) Inventor: Cormac Breatnach, Rathfarnham (IE)

(73) Assignee: INDOMED LIMITED, Sandyford (IE)

( * ) Notice: Subject to any disclaimer, the term of this patent is extended or adjusted under 35 U.S.C. 154(b) by 1126 days.

(21) Appl. No.: 17/286,701

(22) PCT Filed: Oct. 18, 2019

(86) PCT No.: PCT/EP2019/078429
§ 371 (c)(1),
(2) Date: Apr. 19, 2021

(87) PCT Pub. No.: WO2020/079251
PCT Pub. Date: Apr. 23, 2020

(65) Prior Publication Data

US 2021/0338944 A1 Nov. 4, 2021

(30) Foreign Application Priority Data

Oct. 19, 2018 (GB) ..................................... 1817046

(51) Int. Cl.
*A61M 5/42* (2006.01)

(52) U.S. Cl.
CPC ....... *A61M 5/427* (2013.01); *A61M 2205/581* (2013.01); *A61M 2205/582* (2013.01)

(58) Field of Classification Search
CPC ...... A61M 5/427; A61M 5/162; A61M 5/158; A61M 2205/581; A61M 2205/582;
(Continued)

(56) References Cited

U.S. PATENT DOCUMENTS 2,696,695 A * 12/1954 Decker .................. A63H 13/00
242/385.4
5,131,394 A 7/1992 Gehlbach
(Continued)

FOREIGN PATENT DOCUMENTS

DE 102012002412 A1 8/2013
GB 2488810 A 9/2012
(Continued)

OTHER PUBLICATIONS

International Search Report and Written Opinion issued in related Application Serial No. PCT/EP2019/078429 on Jan. 28, 2020.

*Primary Examiner* — Michael J Tsai
*Assistant Examiner* — Justin L Zamory
(74) *Attorney, Agent, or Firm* — Brian J. Colandreo; Jeffrey T. Placker; Holland & Knight LLP

(57) ABSTRACT

This invention relates to a medical device (20, 40, 60) for use in aiding the successful placement of a needle tip in a blood vessel. The medical device comprises a resiliently deformable collapsible body (21) defining a pressure chamber therein. The body further comprises a port (29) for engagement of a hub of a needle, the port defining a fluid passageway from the exterior of the body to the interior of the pressure chamber. The device further comprises means to generate an audible noise (31, 41) upon expansion of the collapsible body from a collapsed configuration to an expanded configuration. In this way, as the tip of the needle enters the lumen of the blood vessel, the collapsible body is configured to transition from a contracted to an expanded configuration, thereby causing the auditory cue. This auditory cue indicates to the medical professional that the tip of the needle is in the lumen of the blood vessel.

7 Claims, 11 Drawing Sheets

(58) Field of Classification Search
CPC ........ A61M 2205/583; A61M 25/0612; A61M 25/0693; A61B 17/3496; A61B 17/3415
See application file for complete search history.

(56) References Cited

U.S. PATENT DOCUMENTS

| | | | | |
|---|---|---|---|---|
| 5,749,857 | A * | 5/1998 | Cuppy | A61M 25/0606 604/161 |
| 10,166,343 | B1 * | 1/2019 | Hunt | A61M 5/3202 |
| 2003/0000402 | A1 * | 1/2003 | Walczak | B41F 27/105 101/375 |
| 2011/0054406 | A1 | 3/2011 | McKinnon | |
| 2013/0338577 | A1 * | 12/2013 | Al-Habaibeh | A61M 5/158 604/164.08 |
| 2014/0271292 | A1 * | 9/2014 | Rowe | F04B 43/08 417/473 |
| 2015/0173661 | A1 * | 6/2015 | Myles | A61B 5/153 600/576 |

FOREIGN PATENT DOCUMENTS

| | | | |
|---|---|---|---|
| WO | 97/25081 | A1 | 7/1997 |
| WO | 2007/032992 | A1 | 3/2007 |

* cited by examiner

MEDICAL DEVICE

RELATED APPLICATIONS

The subject application is a U.S. National Stage application of International Application No. PCT/EP2019/078429, filed on 18 Oct. 2019, which claims the priority of GB Application No.: 1817046.4, filed on 19 Oct. 2018, the contents of which are herein incorporated by reference in its entirety.

TECHNICAL FIELD

This invention relates to a medical device. More specifically, the present invention relates to an aspirator for use in facilitating the successful placement of a needle tip in a blood vessel.

BACKGROUND ART

When accessing central veins during central line insertion it is established practice to mount a needle (classic Seldinger technique) or sheathed needle (modified Seldinger technique) on a syringe and, using ultrasound guidance, advance the needle towards the target vessel whilst aspirating. This application of negative pressure permits early identification of entry of the needle tip into the vessel lumen through the feel of a loss of resistance and the visualisation of blood in the chamber of the syringe. The syringe is then disconnected, the needle held in place and a wire is advanced to secure placement (classic Seldinger). Alternatively, the sheath of the covered needle is advanced to secure initial placement prior to insertion of a wire through the sheath (modified Seldinger).

However, this means of applying negative pressure requires the operator to both grip the barrel of the syringe and pull back on the plunger with the same hand. Consequently, the direction of the needle towards the target is under the control of the large muscle groups of the shoulder and elbow. These muscles are not suited to fine motor control. Furthermore, once entry of the needle tip into the vessel lumen is confirmed, the operator must discontinue using ultrasound and use the hand that was holding the ultrasound probe to advance the sheath into the vessel (modified Seldinger technique).

In order to permit optimal fine motor control, many operators now choose to advance the needle towards the lumen without attaching a syringe. This permits use of the small muscle groups of the hand which are capable of performing very small and precise movements.

The downside to this approach is delayed confirmation of tip placement within the lumen due to the inability to apply suction. This can be particularly problematic where venous pressure is low and passive filling of the needle's chamber is delayed. Relying solely on visual cues can lead to misplacement of hardware as ultrasound may give the impression of the needle tip being within the lumen, whereas the endothelial lining has not been perforated and is merely being tented. Furthermore, in some circumstances, if passive filling of the needle's chamber is delayed, the needle's tip may be advanced too far through the lumen and through the opposite wall of the vessel.

Various devices have been proposed to aid in the successful placement of a needle tip in a blood vessel however heretofore, none have been entirely satisfactory. U.S. Pat. No. 5,314,410, in the name of Marks, discloses an entry indicator device for an arterial or intravenous needle. This device provides a visual indicator, specifically an inflatable balloon, to indicate successful insertion of the needle tip into a blood vessel. However, the device of U.S. Pat. No. 5,314,410 does not appear to provide active suction and requires passive filling. Additionally, the device requires visualization of balloon expansion. Importantly, it is understood that the expanding mushroom-like balloon will prevent a classic Seldinger technique from being performed as the needle would be obstructed.

U.S. Pat. No. 4,108,175, in the name of Orton, discloses a catheter insertion apparatus that may be held in one hand that may also be used to generate a negative pressure to facilitate identification of when the needle tip is in the lumen. The operator of the Orton device should be able to recognize the decrease in resistance and at the same time, a visual indicator of blood being drawn into the chamber will provide a visual indicator that the needle tip is in the lumen. However, the device described in U.S. Pat. No. 4,108,175 is a relatively complex valved configuration that requires a continuous pumping action and requires grasping of the apparatus in the hand with engagement of all fingers and thumb. The movement towards the target remains under the control of the elbow and shoulder muscles.

U.S. Pat. No. 4,487,605, in the name of McGaughey et al discloses a device for catheters that promotes faster flashback (i.e. backflow of blood up through the catheter upon insertion of the needle tip into a lumen acting as a visual indicator) to avoid cannula penetration through the back wall of the vascular structure and into the surrounding tissue. This device is also considered relatively complex in construction with a cam, an internal membrane and a vent.

UK Patent Application Publication No. GB2488810 discloses a fluid vessel communication device with a retractable needle tip. The device is operable to withdraw the tip of a needle from a vessel upon sensing a change in pressure from ambient pressure at the tip of the needle. The device may comprise an additional or alternative alerting means such as an electronic system to sense retraction of the needle and alert the operator by way of a visual or audible indicator. However, it is envisaged that the device described is relatively complex and expensive to manufacture, as well as requiring a power supply in certain embodiments.

Although useful, as indicated above, there are a number of shortcomings of the known solutions. In addition, importantly, each of the proposed solutions relies heavily upon visual cues to confirm when the needle tip is correctly located in the lumen of the blood vessel. This requires the operator to look back and forth between the ultrasound screen and the needle and this can lead to the visual cue being missed and/or the misplacement of hardware.

It is an object of the present invention to provide a medical device that overcomes at least some of the above problems and that offers a useful alternative choice to the consumer.

SUMMARY OF INVENTION

According to the invention there is provided a medical device for use in aiding the successful placement of a needle tip in a blood vessel, the medical device comprising a resiliently deformable collapsible body defining a pressure chamber therein, a biasing means operable to urge the resiliently deformable collapsible body from a collapsed configuration to an expanded configuration, a port for engagement of a hub of a needle, the port defining a fluid passageway from the exterior of the resiliently deformable collapsible body to the interior of the pressure chamber, and in which the medical device further comprises means to generate an audible noise upon expansion of the collapsible body from a collapsed configuration to an expanded configuration.

By having such a device, there is provided an aspirator which may be attached to the needle and that will apply suction without the need for continuous effort from the operator. The operator may rely on their hands rather than the muscles of the shoulder and elbow for the fine motor skills required for placement of the needle tip. This will facilitate easier, more rapid vascular access.

Advantageously, the operator may also keep their focus on the ultrasound screen and will not have to continuously look back and forth between the screen and the device, waiting for a visual cue. By having an audible noise upon expansion of the collapsible body, the operator will be able to hear when the blood is beginning to flow into the device, thereby allowing them to focus on the ultrasound screen. This feature will facilitate not only central venous access but also ultrasound guided peripheral venous and arterial line placement. In addition, the device could be used to facilitate the ultrasound guided aspiration of fluid from other body cavities, for example from a pleural, pericardial or peritoneal collection. Furthermore, by having such a device, it will permit the operator to continue to use ultrasound whilst the sheath is advanced into the vessel (modified Seldinger technique) for safer, more assured hardware placement.

In one embodiment of the invention there is provided a medical device in which the resiliently deformable collapsible body has a bellows-like configuration with a pair of sides and a bladder therebetween.

In one embodiment of the invention there is provided a medical device in which the bladder is constructed from a resiliently deformable material, the natural resilience of the bladder providing the biasing means operable to urge the resiliently deformable collapsible body from a collapsed configuration to an expanded configuration when the bladder is in a collapsed configuration. By having such an arrangement, the expansile properties of the bladder are used to generate negative pressure in the bladder, thereby aspirating as the needle is advanced towards the blood vessel.

In one embodiment of the invention there is provided a medical device in which the bladder is concertinaed.

In one embodiment of the invention there is provided a medical device in which the concertinaed bladder is constructed from a resiliently deformable material, the concertinaed bladder providing the biasing means operable to urge the resiliently deformable collapsible body from a collapsed configuration to an expanded configuration when the concertinaed bladder is in a collapsed configuration. By having such a concertina arrangement, the expansile properties of the bladder are used to generate negative pressure in the bladder, thereby aspirating as the needle is advanced towards the blood vessel.

In one embodiment of the invention there is provided a medical device in which the pair of sides are dimensioned to be grasped between the thumb and the forefinger of an operator. Typically, the sides will not be gripped during insertion. Instead, the sides may be brought together to "lock" the sides of the device in close proximity to each other and/or to flush the device following a failed attempt where blood has been drawn into the chamber. During insertion, it is envisaged that the operator will hold the sheathed needle at a point adjacent the connection between the hub of the needle and the port of the device. This will allow the operator to use the grip with which they are familiar while at the same time allowing the collapsible body to expand.

In one embodiment of the invention there is provided a medical device in which the means to generate an audible noise and vibrations comprises a scraper arm, one end of which is connected to one of the pair of sides of the body and the other, free end of which is inwardly depending towards and for engagement of one or more of the folds of the concertinaed bladder. By having such an arrangement, the friction between the inwardly depending part of the scraper arm and the folds of the concertinaed bladder will generate a "clicking" sound as the bladder expands and the inwardly part of the arm is dragged across the folds. This clicking sound will alert the operator, whose attention is fixed on the ultrasound screen, that entry of the tip into the lumen has occurred and that blood is being aspirated. In one embodiment, there will be provided a flange protruding outwardly from each fold of the bladder. This flange may be of a relatively thin piece of plastic material and may improve the auditory and haptic effect.

In one embodiment of the invention there is provided a medical device in which the free end of the scraper arm is resiliently biased towards the folds of the concertinaed bladder.

In one embodiment of the invention there is provided a medical device in which the scraper arm is dimensioned so that when the bladder is in a fully collapsed configuration, the inwardly depending end of the scraper arm extends beyond and along portion of the other side of the body and is operable to releasably secure the two sides of the body together. In this way, the arm may be used to hold the two sides in a fixed relationship with respect to each other until the needle has been inserted into the patient. In this way, inadvertent release of the sides prior to insertion into the patient will not arise and the device will only start to expand and hence create suction once the arm has been released from holding the other side.

In one embodiment of the invention there is provided a medical device in which one of the inwardly depending end of the scraper arm and the side of the body is provided with a protrusion and the other of the inwardly depending end of the scraper arm and the side of the body is provided with a complementary recess for reception of the protrusion. In this way, a more secure engagement of the scraper arm and the side of the body may be provided to keep the two sides of the body "locked" together until it is desired to release them apart.

In one embodiment of the invention there is provided a medical device in which the scraper arm further comprises a tab extending outwardly therefrom beyond the inwardly depending end of the scraper arm. This is seen as a useful embodiment of the invention. A small tab will allow the operator to "unlock" the two sides of the concertinaed bladder from engagement with each other by sliding their finger or their thumb rearwards and pushing rearwardly on the tab to release the scraper arm from one of the sides of the body.

In one embodiment of the invention there is provided a medical device in which the port is angularly offset from a longitudinal axis of the resiliently deformable collapsible body. This is seen as a particularly useful aspect of the invention. By having the port angularly offset from the longitudinal axis of the resiliently deformable body, the expansion of the resiliently deformable collapsible body will not be impeded by the patient. Furthermore, this will enable the device and the needle attached thereto to be introduced at a shallow angle to the patient's skin. This may be particularly relevant and advantageous when attempting to introduce a needle into a jugular vein or other vein in the patient's neck.

In one embodiment of the invention there is provided a medical device in which the port is provided with a side port branching off therefrom, the side port having a closure thereon. Again, this is seen as a particularly useful aspect of the invention. The side port may be used for the introduction of wire through the side port, through the port and along the needle allowing the fast execution of the Seldinger or modified Seldinger technique.

In one embodiment of the invention there is provided a medical device in which the closure comprises a valve. It is important that it a valve is used, that the valve will not allow air intake into the vein or into the resiliently deformable collapsible body pressure chamber while the device is being inserted into a patient. Accordingly, the valve strength will be sufficiently strong that it will act against air intake until the tip of the needle is inside the vessel at which stage the valve strength may be overcome in order to allow insertion of a wire.

In one embodiment of the invention there is provided a medical device in which the closure comprises an end cap. A cap may be provided instead of or in addition to a valve.

In one embodiment of the invention there is provided a medical device in which the means to generate an audible noise comprises a surface coating on the folds of the concertinaed bladder that generate a noise when two abutting surfaces are separated apart from each other. This is seen as a useful alternative way to generate the noise. For example, if one of the surfaces of a fold has an adhesive coating thereon to form a loose bond with the surface of an adjacent fold, as the two folds and by extension surfaces are separated from each other, they will cause a tearing sound as they are separated. This sound may be interpreted by the operator as the expansion of the bladder and the location of the lumen by the needle tip as blood flows into the bladder.

In one embodiment of the invention there is provided a medical device in which the means to generate an audible noise comprises a spring force holding the folds of the concertinaed bladder together that generate a noise when two sides of a fold are separated apart from each other. Effectively, the folds act akin to an over centre spring and will "pop" as they are separated apart from each other.

In one embodiment of the invention there is provided a medical device in which the port is dimensioned to form a push fit in the hub of a needle.

In one embodiment of the invention there is provided a medical device in which the port is provided with a luer lock attachment for engagement of the hub of a needle.

In one embodiment of the invention there is provided a medical device in which there is provided a spring operable to return the body from a collapsed configuration to an expanded configuration. This may be provided instead of or in addition to a natural resilience of the body.

In one embodiment of the invention there is provided a medical device in which there is provided means to generate a haptic feedback upon expansion of the collapsible body from a collapsed configuration to an expanded configuration. The means to generate the haptic feedback will preferably also be provided by way of the means to generate an audible noise. For example, the scraper arm may also provide vibrations that may be sensed by the operator as well as the sound generated thereby.

In one embodiment of the invention there is provided a medical device in which there is provided means to releasably secure the resiliently deformable collapsible body in a collapsed configuration. This may be achieved in a number of ways. For example, if a scraper arm is provided, the scraper arm may be dimensioned so that the inwardly depending free end of the arm extends beyond the rear surface of the other side of the device to hold the two sides of the device together and the resiliently deformable collapsible body, for example the bladder, in a collapsed configuration therebetween. Alternatively, there may be a strap mounted on one side of the device with a button, a clasp, a magnet or other arrangement for engagement of a complementary member on the other side of the device to temporarily hold the body in a collapsed configuration. A pair of arms or flexible members, one on each side of the device, with complementary engagement members on the arms could be provided to hold the resiliently deformable collapsible body in a collapsed configuration.

In one embodiment of the invention there is provided, in combination, a medical device as claimed in any of the claims and a needle having a hub, a shaft having a lumen extending the length thereof, the proximal butt end of the shaft being in engagement with the hub and the distal, free end of the shaft terminating in a bevel. By having such a combination, the needle may come pre-packaged with the aspirator ready for use by medical personnel. The combination may be used as part of a classic Seldinger technique.

In one embodiment of the invention there is provided, in combination, the medical device, a needle and a sheath for the needle. The combination may be used as part of a modified Seldinger technique.

BRIEF DESCRIPTION OF THE DRAWINGS

The invention will now be more clearly understood from the following description of some embodiments thereof given by way of example only with reference to the accompanying drawings, in which:—

DETAILED DESCRIPTION OF THE DRAWINGS

Figure 1:
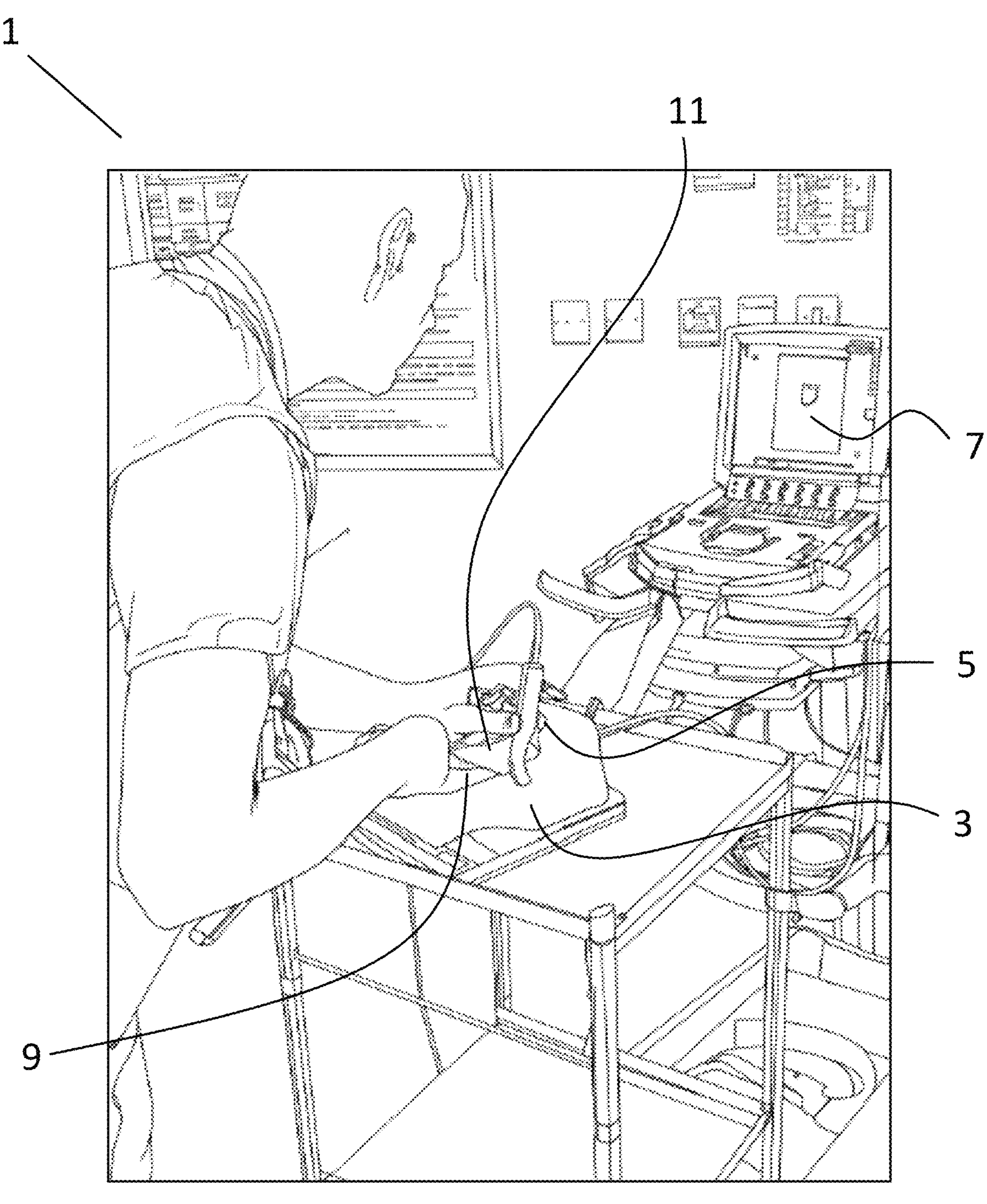
FIG. 1 is a photograph of a medical professional demonstrating a technique known in the art on a test apparatus.

Referring to FIG. 1, there is shown a photograph of a medical professional, indicated generally by the reference numeral 1, demonstrating a technique known in the art for performing a central line insertion on a test apparatus 3. In their left hand, the medical professional is holding an ultrasound probe 5 whilst viewing the ultrasound of the test area on an ultrasound monitor 7. In their right hand, the medical professional holds a syringe 9 with a needle 11 thereon.

Figure 2:
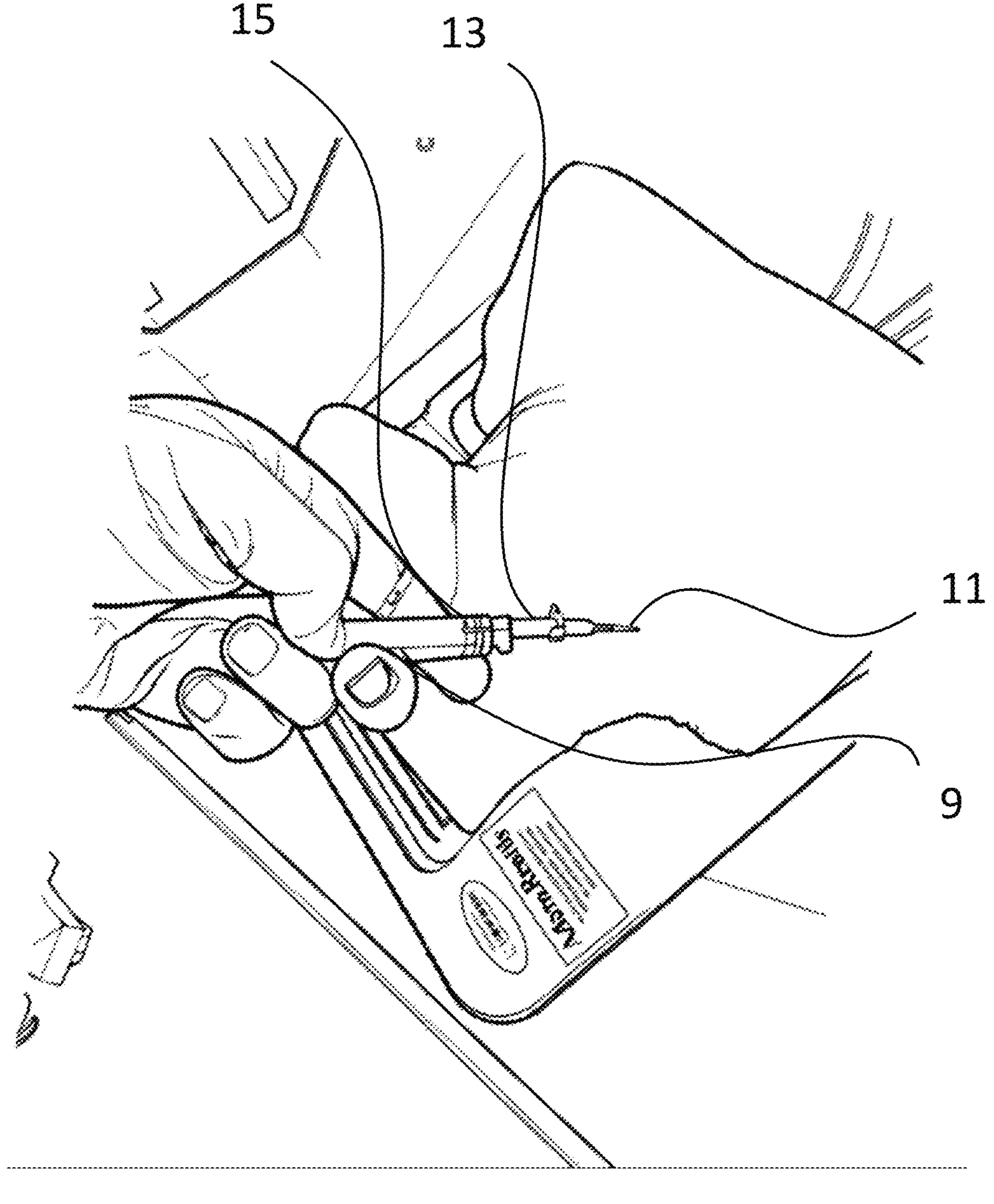
FIG. 2 is a photograph of a medical professional demonstrating a technique known in the art on a test apparatus.

Referring to FIG. 2, there is shown an enlarged photograph of the medical professional's grip on the syringe as they perform the known technique for inserting a central line. For ease of understanding and so as not to obscure features, the syringe 9 is now shown in the left hand of the medical professional. The medical professional grasps the chamber 13 of the syringe 9 between their thumb, index and middle fingers and operates the plunger 15 of the syringe 9 using their remaining fingers. The plunger of the syringe is slowly extracted from the chamber. As the end of the needle 11 is located inside the test subject in the absence of air, a partial vacuum is created inside the syringe chamber 13 between the internal end of the plunger 15 and the needle 11. When the tip of the needle is inserted into the lumen of the blood vessel, the operator of the needle will experience a reduction in resistance and furthermore, the partial vacuum will act to draw blood inwardly from the vein into the syringe chamber. The appearance of blood in the syringe and the reduction of resistance will be sufficient to indicate that the tip of the needle is in the lumen of the blood vessel. Once in position, the remaining steps of the Seldinger technique may be performed.

It can be seen that in such a configuration shown in FIG. 2, fine movement of the hand to position the needle is impractical. Referring once again to FIG. 1, it will be appreciated that the muscles in the shoulder and the elbow region are used to insert the needle as the hand muscles are used to grip the syringe and operate the plunger. The shoulder and elbow muscles are not however suitable for fine adjustment, thereby increasing the difficulty in correct placement of the tip of the needle.

Figure 3:
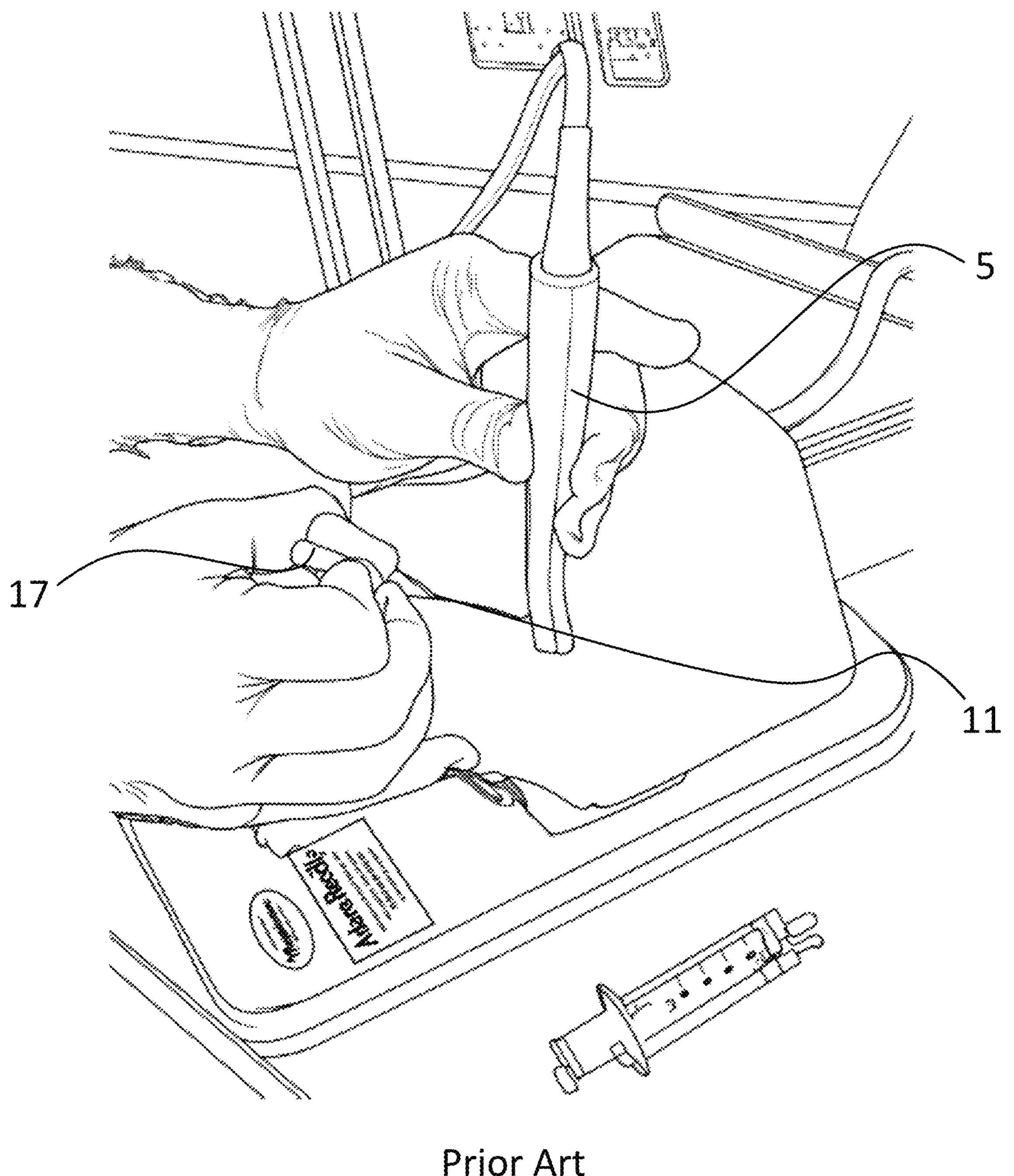
FIG. 3 is a photograph of a medical professional demonstrating an alternative technique known in the art on a test apparatus.
Figure 4:
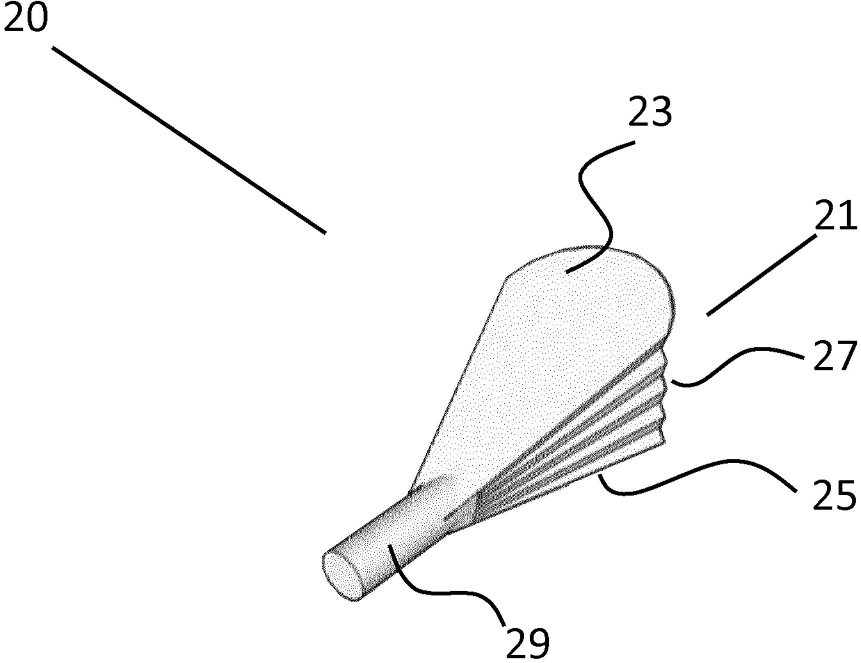
FIG. 4 is a front perspective view of a first embodiment of medical device according to the invention.

Referring to FIG. 3, there is shown a photograph of an alternative technique for inserting a central line known in the art. In the photograph, the medical professional holds the probe 5 of the ultrasound in their left hand and a needle 11 in their right hand. Effectively, the needle is provided without the syringe. Accordingly, the medical professional can grasp the hub 17 of the needle between their thumb and forefinger and use their hand muscles to more accurately position the tip of the needle. This grip will permit the operator to advance the sheath using the index or middle finger of the same hand. This also makes positioning the tip of the needle easier than the technique described with reference to FIGS. 1 and 2 as the muscles of the hand, rather than the muscles of the shoulder and elbow, are used for needle tip positioning.

However, as there is no syringe provided in the technique described with reference to FIG. 3, there is no vacuum created with which to draw in blood into the needle and provide an indication to the medical professional that the tip of the needle is in fact inside the lumen of the blood vessel. Instead, the medical professional must guide the tip of the needle using ultrasound guidance to a position where they believe that the tip of the needle is inserted into the blood vessel and wait until blood begins to enter into the needle. In cases where the blood pressure is low, this can take a significant length of time which is highly undesirable. This delay can lead to the medical professional believing that the tip of the needle is not correctly placed inside the lumen of the blood vessel and either progressing the needle further thereby penetrating through the other side wall of the blood vessel or making a second or subsequent attempt to locate the tip of the needle in the blood vessel. The present invention attempts to address the shortcomings of the known methods and apparatus.

Figure 9:
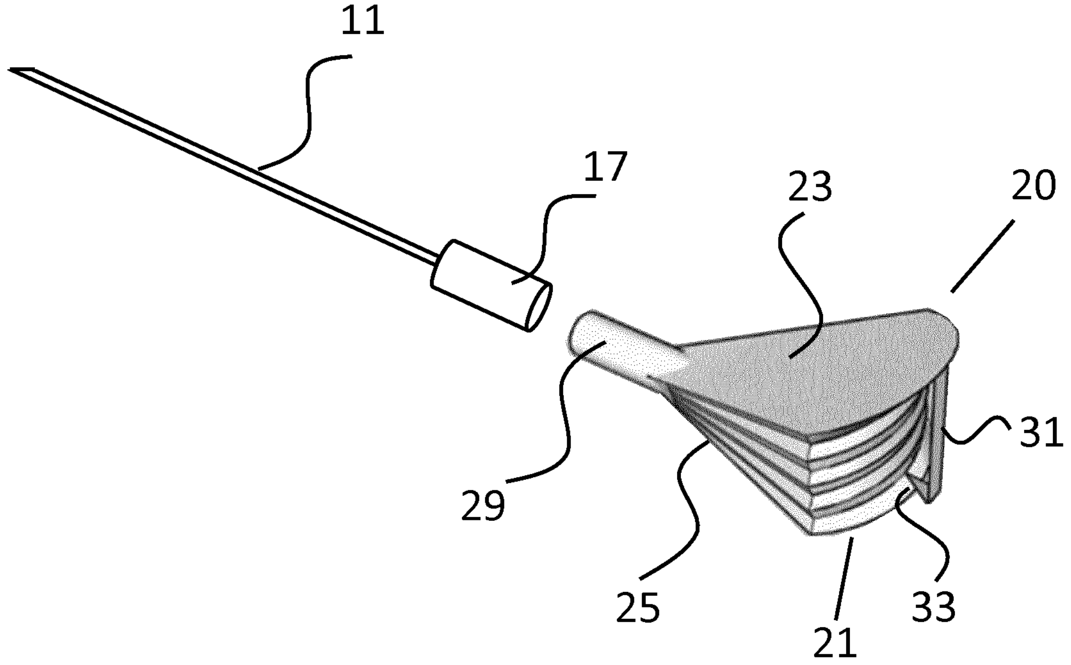
FIG. 9 is a perspective view of the medical device being introduced into a needle.

Referring now to FIGS. 4 to 9 inclusive, there are shown a number of representations of a first embodiment of a medical device according to the invention, indicated generally by the reference numeral 20. The medical device 20 comprises a resiliently deformable, collapsible body 21 defining a pressure chamber (not shown) therein. In the embodiment shown, the body 21 is provided in the form of a bellows comprising a pair of sides 23, 25, and a concertinaed bladder 27 therebetween. The construction is such that the concertinaed bladder is in a state where it urges the sides 23, 25 apart. The body further comprises a port 29 defining a fluid passageway from the exterior of the body to the interior of the pressure chamber. The port 29 is dimensioned to engage the hub of a needle (as illustrated in FIG. 9 in which the port is about to be introduced into the hub of the needle and will form a push fit in the hub).

Figure 5:
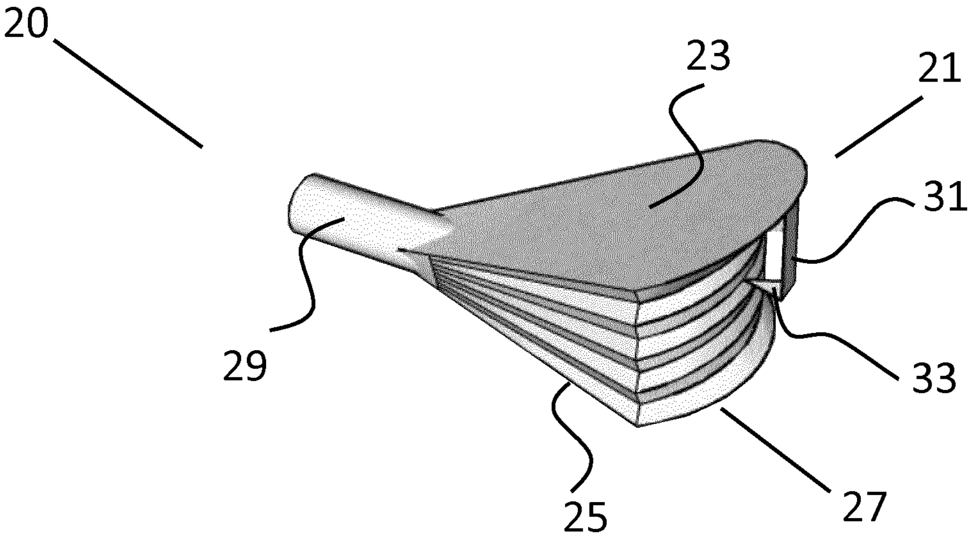
FIG. 5 is a rear perspective view of the medical device of FIG. 4.
Figure 6:
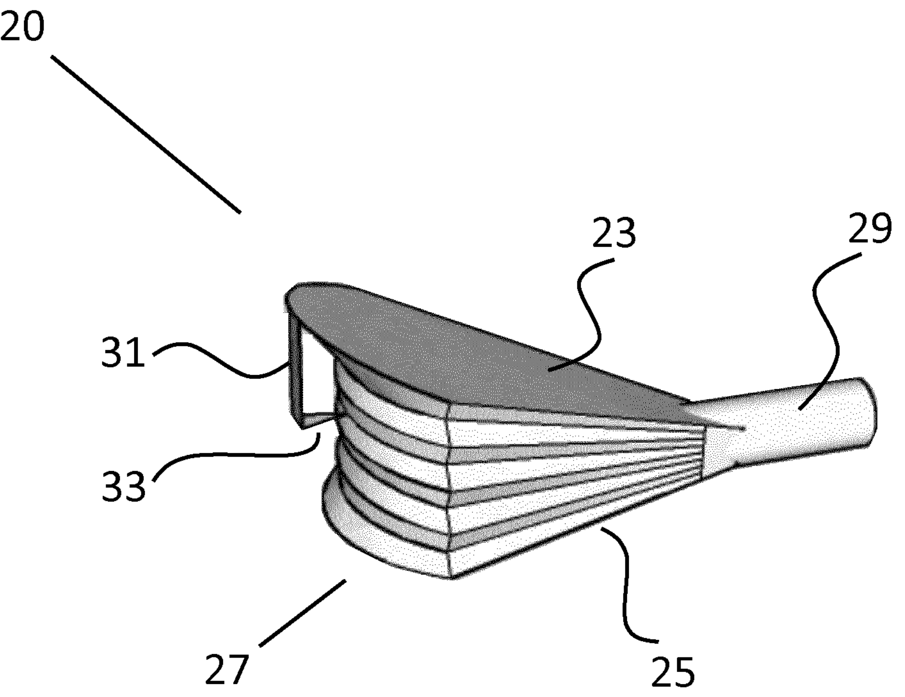
FIG. 6 is another rear perspective view of the medical device of FIG. 4.
Figure 7:
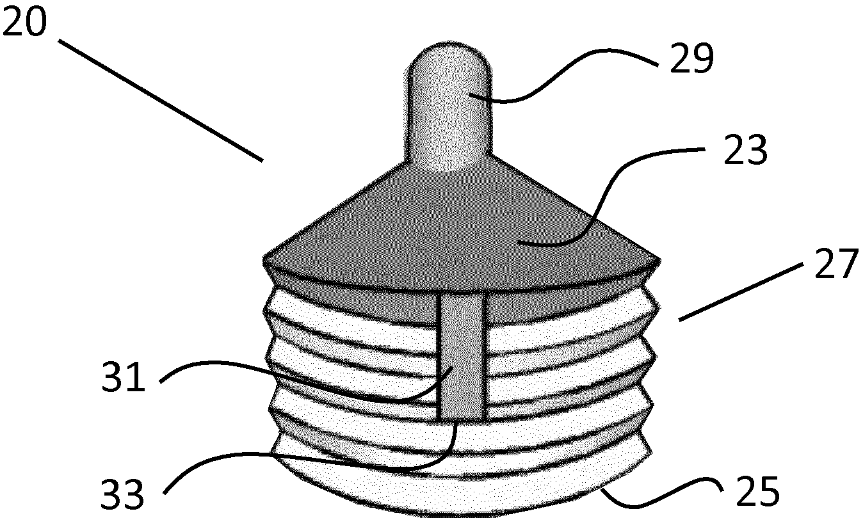
FIG. 7 is a rear view of the medical device of FIG. 4.
Figure 8:
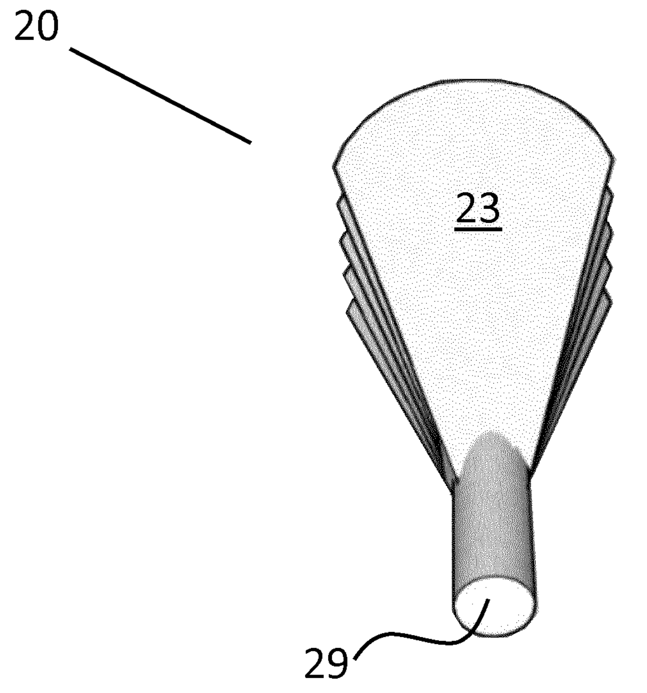
FIG. 8 is a front view of the medical device of FIG. 4.

Referring specifically to FIGS. 5 to 7, there is shown a scraper arm 31. The scraper arm 31 is connected at one of its ends to one of the sides 23. The other, free, end 33 of the scraper arm is cranked inwardly towards the folds of the concertinaed bladder. The free end 33 of the scraper arm contacts against the folds of the concertinaed bladder. As the bladder expands from a contracted configuration with the folds of the bladder in close proximity to each other, the free end 33 of the scraper arm will scrape over the folds causing vibrations and a "clicking" noise as the bladder expands.

In use, the port 29 is introduced into the hub 17 of the needle 11. Instead of providing a push fit, the port may have a luer lock component for complementary engagement of a luer lock fitting on the hub 17 of the needle. Once the needle 11 and the medical device are in engagement, the sides 23, 25 are grasped between the operators thumb and forefinger and brought towards each other. This will expel any air from the internal pressure chamber of the resiliently deformable, collapsible body 21. In the compressed state, the inwardly depending end of the scraper arm will extend around the lower side 25 and engage the face of the lower side, thereby holding the sides 23 and 25 of the collapsible body in a fixed relationship with respect to each other and also the concertinaed bladder in a compacted configuration. If desired, the sides can be brought together before connection of the needle to the hub.

The operator will then grasp the hub of the needle between the thumb and the forefinger of their hand and the tip of the needle is then inserted into the patient and the free end of the scraper arm is moved free of the side 25. The sides 23, 25 will move slightly apart from each other under the resilience of the concertinaed bladder, thereby forming a partial vacuum inside the body in the pressure chamber. The tip of the needle is then further guided into the patient, under ultrasound guidance, towards the blood vessel. The concertinaed bladder will not expand further as the tip of the needle passes through muscle and tissue. It will be appreciated that the device may be easily "flushed" by squeezing the two sides together. Furthermore, advantageously, the device is formed as a single unit.

When the tip of the needle enters the blood vessel, the partial vacuum will cause blood to be drawn into the pressure chamber of the medical device. When the tip of the needle is located inside the fluid inside the lumen of the blood vessel, the resiliently deformable bladder will be able to expand further, drawing more blood into the pressure chamber as the bladder expands. Most importantly, as the bladder expands, the free end 33 of the scraper arm will scrape against the folds of the concertinaed bladder causing vibrations and a clicking noise. This clicking noise will indicate to the medical professional that the bladder is expanding and by extension that the tip of the needle is in the lumen of the blood vessel. This auditory and haptic cue will enable the medical professional to keep their eyes on the ultrasound monitor throughout. Once the medical professional is confident that the tip of the needle is located inside the lumen of the blood vessel, they can obtain further assurance by examining the presence of blood in the needle hub and/or the medical device (if constructed at least in part from a transparent/translucent material).

Referring now to FIGS. 10 to 15 inclusive, there is shown a second embodiment of medical device, indicated generally by the reference 40, where like parts have been given the same reference numeral as before. The medical device 40 also comprises a resiliently deformable, collapsible body 21 defining a pressure chamber therein. The body 21 is provided in the form of a bellows comprising a pair of sides 23, 25, and a concertinaed bladder 27 therebetween. The construction is such that the concertinaed bladder urges the sides 23, 25 apart when the concertinaed bladder is in a collapsed configuration. The body 21 further comprises a port 29 dimensioned to engage the hub of a needle and defining a fluid passageway from the exterior of the body to the interior of the pressure chamber. As before, there is further provided a scraper arm 41, the scraper arm 41 being connected at one of its ends to one of the sides 23 and the other, free, end 33 of the scraper arm is cranked inwardly towards the folds of the concertinaed bladder. The free end 33 of the scraper arm contacts against the folds 43 of the concertinaed bladder so that as the bladder expands from a contracted configuration with the folds of the bladder in close proximity to each other to an expanded configuration, the free end 33 of the scraper arm 41 will scrape over the folds causing a "clicking" noise and vibrations as the bladder expands. More specifically, the free end of the scraper arm contacts against a flange 45 of each fold 43.

Figure 10:
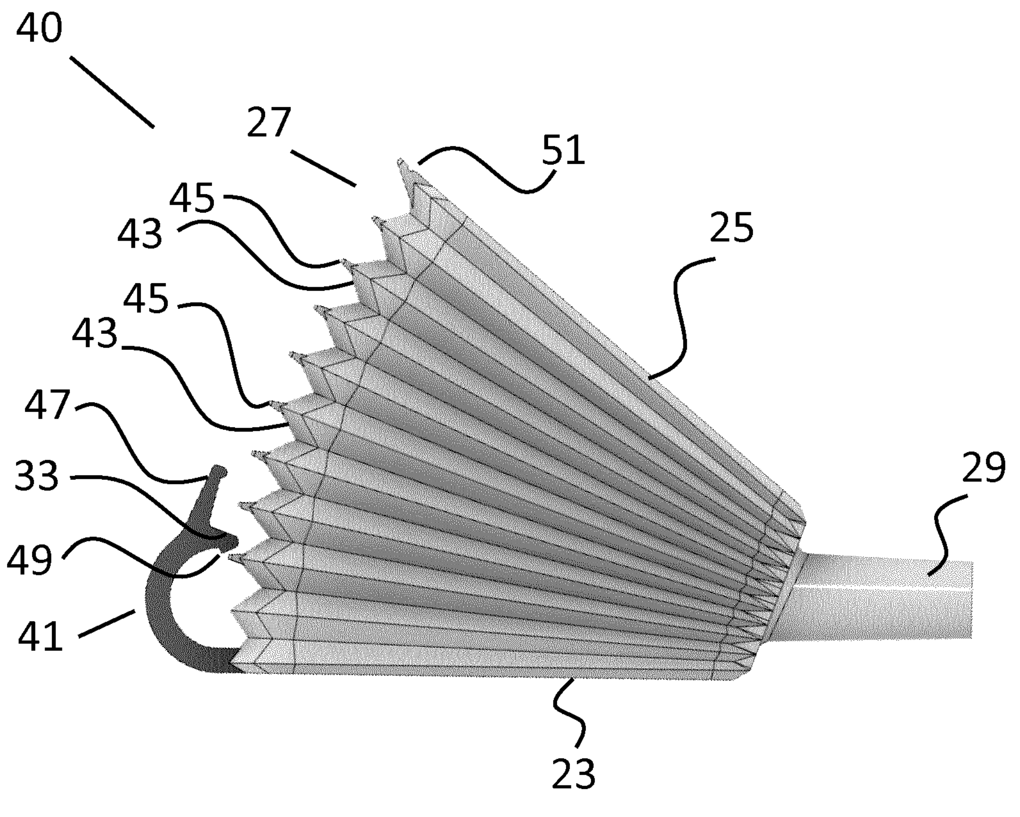
FIG. 10 is a side view of a second embodiment of medical device according to the invention.
Figure 11:
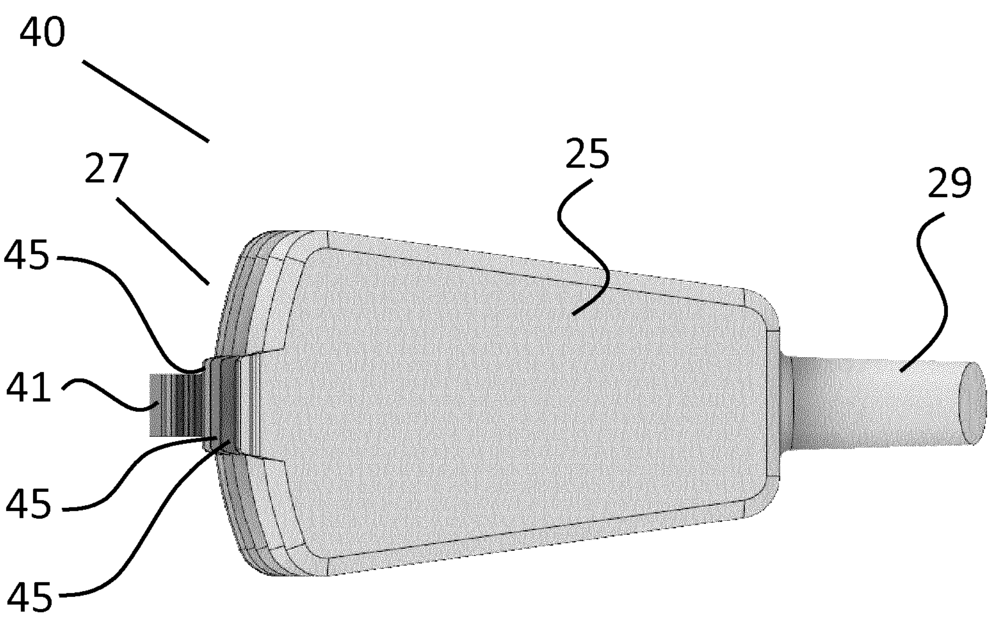
FIG. 11 is a top plan view of the medical device of FIG. 10.
Figure 12:
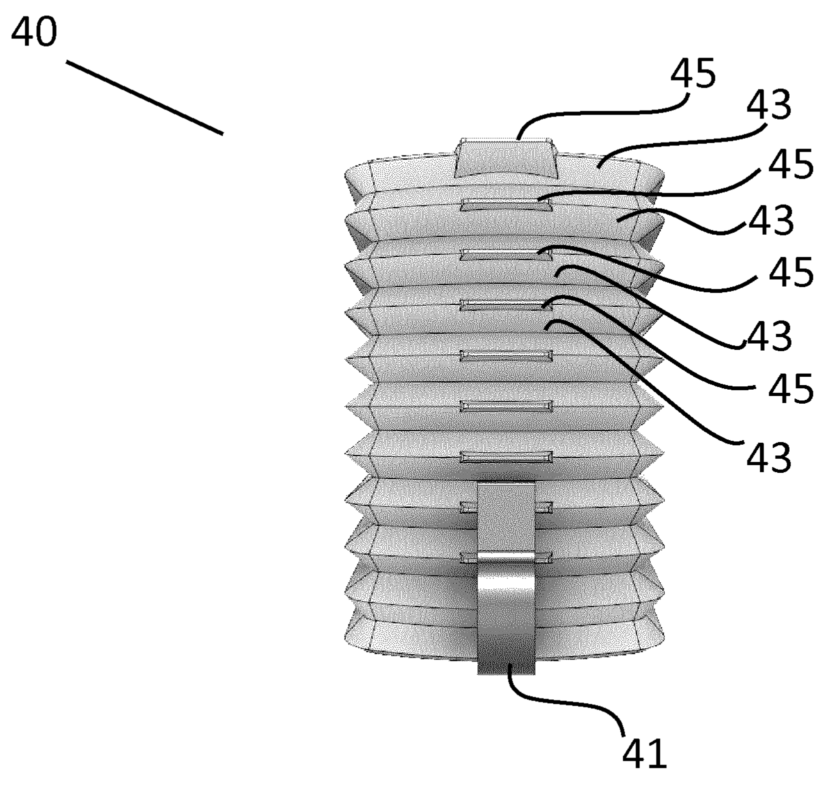
FIG. 12 is a rear view of the medical device of FIG. 10.
Figure 13:
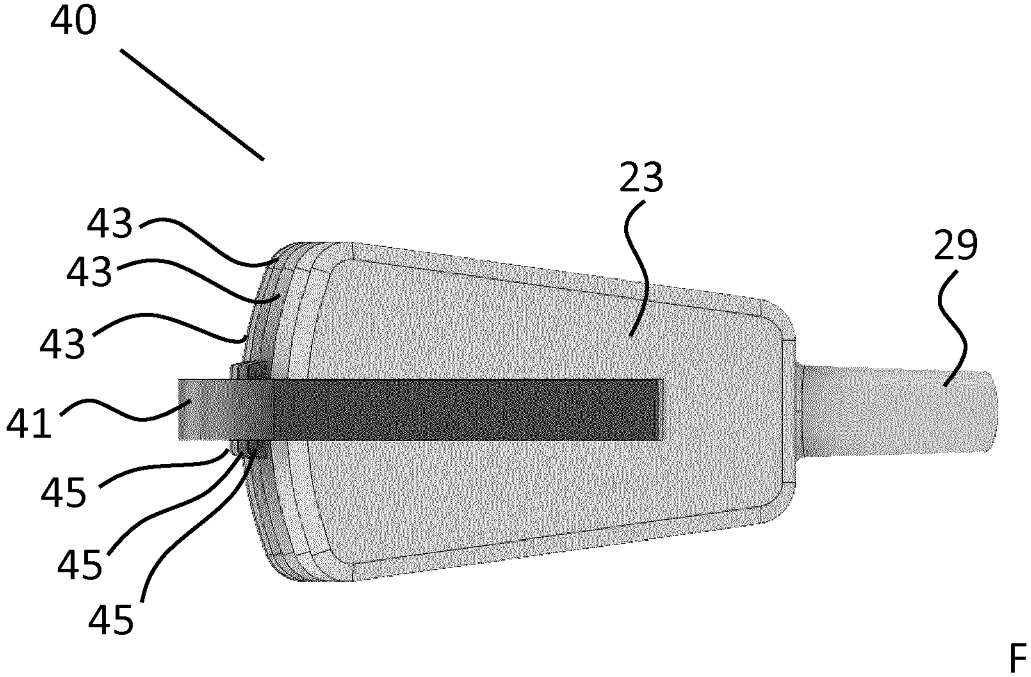
FIG. 13 is a view from underneath of the medical device of FIG. 10.
Figure 14:
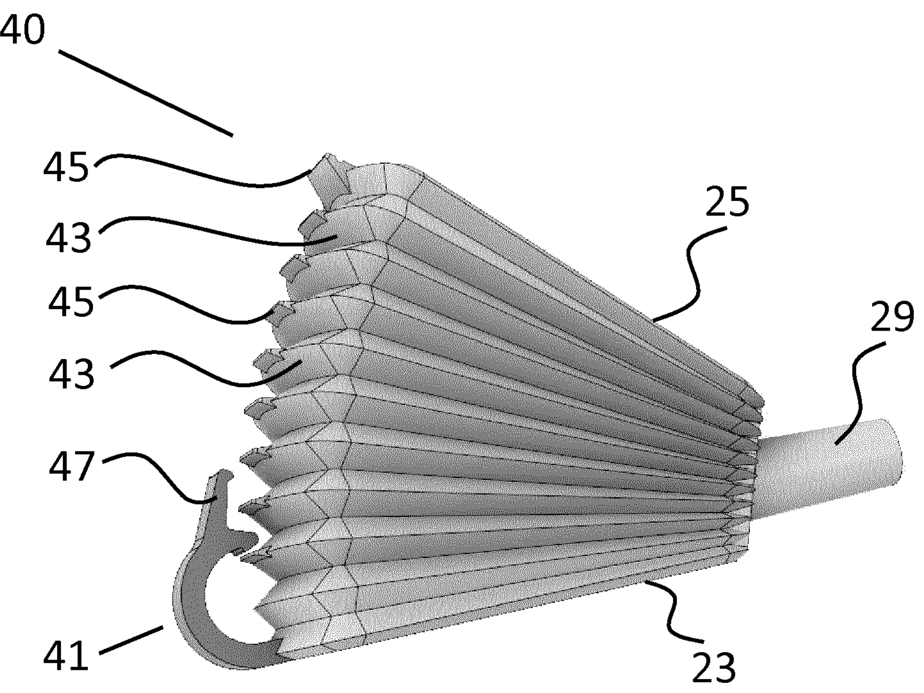
FIG. 14 is a rear perspective view of the medical device of FIG. 10.
Figure 15:
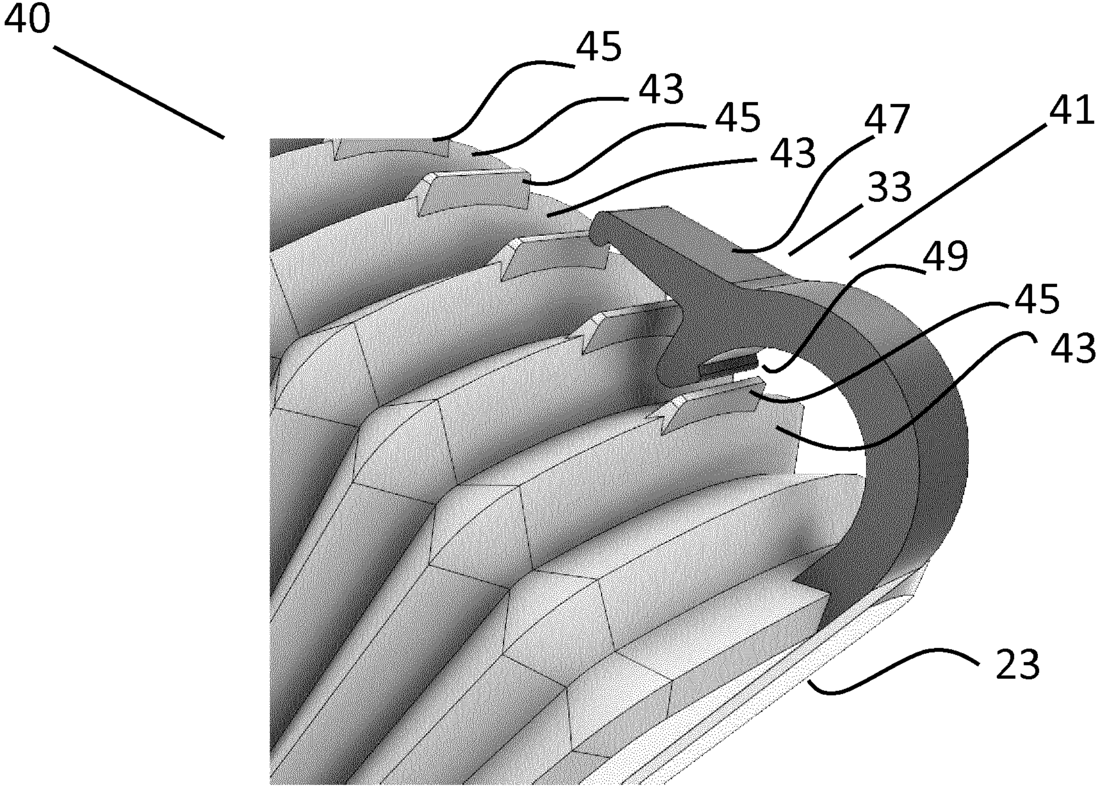
FIG. 15 is an enlarged view of the scraper arm and portion of the resiliently deformable collapsible body.

Referring specifically to FIG. 10, it can be seen that the scraper arm 41 differs from the scraper arm 31 of the first embodiment shown in FIGS. 3 to 9 inclusive in that the scraper arm 41 comprises a tab 47 extending upwardly from the free end 33 of the scraper arm 41. In use, when an operator has inserted the tip of the needle (not shown) into the patient and wishes to release the scraper arm 41 from holding the two sides 23, 25 of the resiliently deformable collapsible body together, the operator slides their finger or a thumb rearwards to press against the tab 47 and release the inwardly depending end 33 from the side 25 of the resiliently deformable collapsible body. The resiliently deformable collapsible body will expand to a degree until the side 25 is free of the free end 33 of the scraper arm 41.

In the embodiment shown, the orientation is such that the tab 47 will, in use, be to the side of the device 40 remote from the patient for ease of access. In this way, if the port 29 or the hub of the needle is held between the operator's thumb and their middle finger, the operator's index finger may be slid rearwards to disengage the scraper arm 41 from the side of the resiliently deformable collapsible body.

In addition, the inwardly depending end 33 of the scraper arm 41 is provided with a protrusion 49 and the side 25 of the body is provided with a complementary recess 51 for reception of the protrusion 49. This will provide a more secure engagement between the scraper arm and the side when the two sides of the resiliently deformable collapsible body are being held together.

In addition to the forgoing, it can be seen that the port 29 of the medical device 40 is angularly offset from a longitudinal axis of the resiliently deformable collapsible body. This is envisaged to be advantageous as it will allow the expansion of the resiliently deformable collapsible body without it being impeded by the patient. It will also enable the device and the needle attached thereto to be introduced at a shallower angle to the patient's skin than would otherwise be the case which has advantages for needle tip placement. Finally, this configuration may be particularly relevant and advantageous when attempting to introduce a needle into a jugular vein or other vein in the patient's neck where space is limited, and it is desirable to have a shallow angle of attack. It is envisaged that the port could be angularly offset from the longitudinal axis of the resiliently deformable collapsible body by of the order of 5° to 75°, preferably between 10° to 70°, more preferably between 20° to 60°. It is envisaged that the ideal angular offset could be of the order of 45°.

Figure 16:
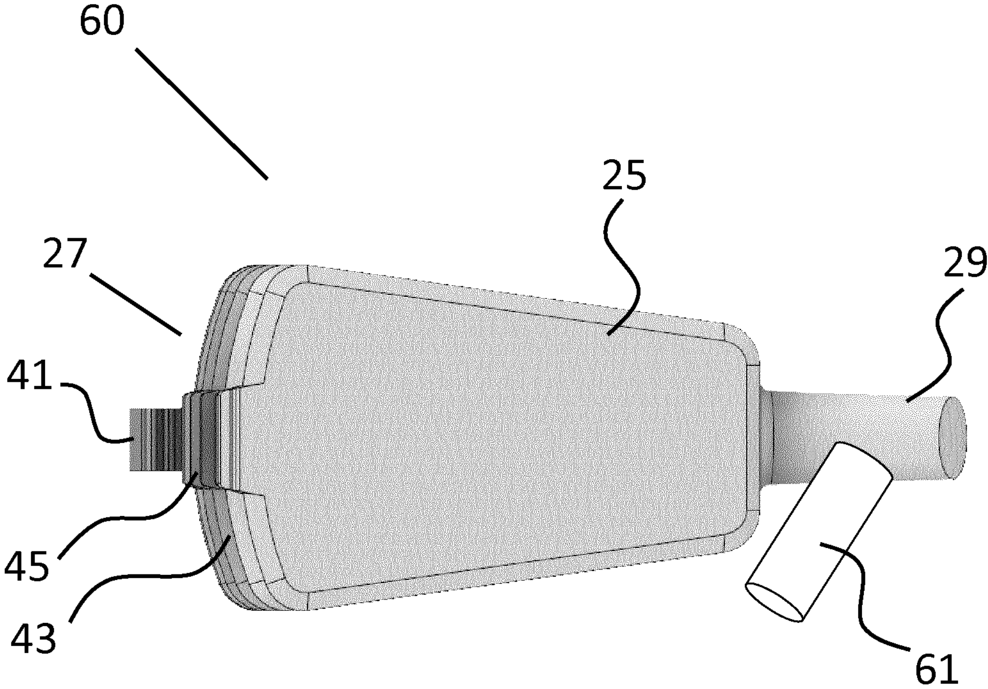
FIG. 16 is a top plan view of a third embodiment of medical device according to the invention.

Referring now to FIG. 16, there is shown a third embodiment of medical device, indicated generally by the reference 60, where like parts have been given the same reference numeral as before. The medical device 60 is similar in construction to the medical device 40 illustrated in FIGS. 10 to 15 inclusive with the exception that the medical device 60 comprises a side port 61 branching off the port 29. The side port 61 may be used for the introduction of a wire through the side port 61 and into the patient's vessel when the tip of the needle (not shown) has been introduced into the patient. The side port 61 may have a valve and/or a removable end cap at its free end remote from the port 29 that will prevent ingress of air into the patient or into the pressure chamber before the tip of the needle is in place in the vessel.

It will be understood that various modifications could be made to the constructions described. For example, it is envisaged that the resiliently deformable body may take a form other than bellows-shaped. For example, the resiliently deformable body may be balloon-shaped or indeed pillow-shaped. The balloon-shaped or pillow-shaped resiliently deformable body may be sandwiched between two sides 23, 25 such as those shown in the embodiments hereinbefore described.

Furthermore, instead of a scraper arm, other means could be provided for generating a sound on the expansion of the resiliently deformable body. For example, if there is a concertina arrangement, the sides of the folds may be provided with an adhesive material so that as the sides separate, there is a tearing sound as the side come apart from each other. Similarly, the sides of the folds could act in a manner similar to over-centre springs in that they would "pop" as they expand. Alternatively, a sensor and a sensor target could be provided, one on either side of the bellows-like body and effectively a capacitive sensor could be provided. This however would require a buzzer or like electrically powered device and a power supply and is not therefore preferred. Ideally, the means to generate an audible noise of the device will do so mechanically. In other words, it will be configured to create a noise without any external electrical power supply. Instead, the noise will be created by two components moving against or apart from each other such as the scraper arm impacting and/or releasing from a fold of the concertinaed bladder.

It is envisaged that the means for providing the sound as the resiliently deformable body expands could comprise an arm mounted on one side of the device with a plurality of protrusions such as bosses or "sharks teeth" formed along a surface thereof. The arm could be led through a complementary groove or an aperture in the opposite side of the device with the protrusions abutting against the other side of the device. In this way, as the sides of the device are separated apart from each other, the arm will be withdrawn from the complementary groove or aperture and the protrusions on the arm will rub against the side wall of the aperture of groove, resulting in a noise that can be heard by the operator of the device and preferably also a vibration that may be sensed by the operator of the device.

It is envisaged that the medical device could be provided with a needle and, if desired, a sheath on the needle so that it may be used in the Seldinger or modified Seldinger techniques. The components could be provided already constructed and packaged if desired with wire and any other tubing or like components required to carry out the procedure. It will be understood that the present invention has been described in terms of inserting a central line however it is not limited to such a procedure as would be readily understood by the skilled addressee. It is envisaged that the port of the medical device may be permanently connected to the hub of a needle.

Throughout the specification, reference is made to the medical device having a body that is resiliently deformable and there being provided a biasing means operable to urge the resiliently deformable collapsible body from a collapsed configuration to an expanded configuration. The biasing means could be provided by way of a spring such as, but not limited to a helical spring or a leaf spring that could be located internal or external the body, for example pressing against the two sides 23, 25, urging them apart. Preferably however, the biasing means operable to urge the resiliently deformable collapsible body from a collapsed configuration to an expanded configuration will be provided by the natural elastic properties of the body itself, that when compressed into a collapsed configuration, will have a tendency to urge the sides 23, 25 of the body apart towards an expanded configuration. To this end, the body may be constructed from a suitable material with these elastic properties.

In this specification the terms "comprise, comprises, comprised and comprising" and the terms "include, includes, included and including" are all deemed interchangeable and should be afforded the widest possible interpretation.

The invention is not limited to the embodiments hereinbefore described but may be varied in both construction and detail within the scope of the claims.

The invention claimed is:

1. A medical device for use in aiding the successful placement of a needle tip in a blood vessel, the medical device comprising a resiliently deformable collapsible body defining a pressure chamber therein, a biasing means operable to urge the resiliently deformable collapsible body from a collapsed configuration to an expanded configuration, a port for engagement of a hub of a needle, the port defining a fluid passageway from the exterior of the resiliently deformable collapsible body to the interior of the pressure chamber, and in which the medical device further comprises means to generate an audible noise upon expansion of the collapsible body from a collapsed configuration to an expanded configuration, in which the resiliently deformable collapsible body has a bellows-like configuration with a pair of sides and a bladder therebetween, in which the bladder is concertinaed and in which the means to generate an audible noise comprises a scraper arm, one end of which is connected to one of the pair of sides of the body and the other, free end of which is inwardly depending towards and for engagement of one or more of the folds of the concertinaed bladder.

2. The medical device as claimed in claim 1 in which the free end of the scraper arm is resiliently biased towards the folds of the concertinaed bladder.

3. The medical device as claimed in claim 1 in which the scraper arm is dimensioned so that when the concertinaed bladder is in a fully collapsed configuration, the inwardly depending end of the scraper arm extends beyond and along a portion of the other side of the body and is operable to releasably secure the two sides of the body together.

4. The medical device as claimed in claim 3 in which one of the inwardly depending end of the scraper arm and the side of the body is provided with a protrusion and the other of the inwardly depending end of the scraper arm and the side of the body is provided with a complementary recess for reception of the protrusion.

5. The medical device as claimed in claim 3 in which the scraper arm further comprises a tab extending outwardly therefrom beyond the inwardly depending end of the scraper arm.

6. A medical device for use in aiding the successful placement of a needle tip in a blood vessel, the medical device comprising a resiliently deformable collapsible body defining a pressure chamber therein, a biasing means operable to urge the resiliently deformable collapsible body from a collapsed configuration to an expanded configuration, a port for engagement of a hub of a needle, the port defining a fluid passageway from the exterior of the resiliently deformable collapsible body to the interior of the pressure chamber, and in which the medical device further comprises means to generate an audible noise upon expansion of the collapsible body from a collapsed configuration to an expanded configuration, in which the resiliently deformable collapsible body has a bellows-like configuration with a pair of sides and a bladder therebetween, in which the bladder is concertinaed and in which the means to generate an audible noise comprises a surface coating on the folds of the concertinaed bladder that generate a noise when two abutting surfaces are separated apart from each other.

7. A medical device for use in aiding the successful placement of a needle tip in a blood vessel, the medical device comprising a resiliently deformable collapsible body defining a pressure chamber therein, a biasing means operable to urge the resiliently deformable collapsible body from a collapsed configuration to an expanded configuration, a port for engagement of a hub of a needle, the port defining a fluid passageway from the exterior of the resiliently deformable collapsible body to the interior of the pressure chamber, and in which the medical device further comprises means to generate an audible noise upon expansion of the collapsible body from a collapsed configuration to an expanded configuration, in which the resiliently deformable collapsible body has a bellows-like configuration with a pair of sides and a bladder therebetween, in which the bladder is concertinaed and in which the means to generate an audible noise comprises a spring force holding the folds of the concertinaed bladder together that generate a noise when two sides of a fold are separated apart from each other.

* * * * *